United States Patent
Parihar et al.

(10) Patent No.: US 9,314,308 B2
(45) Date of Patent: Apr. 19, 2016

(54) ROBOTIC ULTRASONIC SURGICAL DEVICE WITH ARTICULATING END EFFECTOR

(71) Applicant: Ethicon Endo-Surgery, Inc., Cincinnati, OH (US)

(72) Inventors: Shailendra K. Parihar, Mason, OH (US); Foster B. Stulen, Mason, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 236 days.

(21) Appl. No.: 13/798,766

(22) Filed: Mar. 13, 2013

(65) Prior Publication Data

US 2014/0276931 A1    Sep. 18, 2014

(51) Int. Cl.
| A61B 19/00 | (2006.01) |
| A61B 17/32 | (2006.01) |
| A61B 18/14 | (2006.01) |
| A61B 17/00 | (2006.01) |
| A61B 17/29 | (2006.01) |

(52) U.S. Cl.
CPC ..... *A61B 19/2203* (2013.01); *A61B 17/320092* (2013.01); *A61B 18/1445* (2013.01); *A61B 2017/00309* (2013.01); *A61B 2017/00327* (2013.01); *A61B 2017/00477* (2013.01); *A61B 2017/2929* (2013.01); *A61B 2019/2223* (2013.01); *A61B 2019/2234* (2013.01)

(58) Field of Classification Search
CPC ................. A61B 19/2203; A61B 2019/2242; A61B 2019/2234; A61B 19/22
See application file for complete search history.

(56) References Cited

U.S. PATENT DOCUMENTS

| 5,322,055 | A | 6/1994 | Davison et al. |
| 5,792,135 | A | 8/1998 | Madhani et al. |
| 5,817,084 | A | 10/1998 | Jensen |
| 5,873,873 | A | 2/1999 | Smith et al. |
| 5,878,193 | A | 3/1999 | Wang et al. |
| 5,897,523 | A | 4/1999 | Wright et al. |
| 5,980,510 | A | 11/1999 | Tsonton et al. |
| 5,989,264 | A | 11/1999 | Wright |
| 6,063,098 | A | 5/2000 | Houser et al. |

(Continued)

FOREIGN PATENT DOCUMENTS

WO    WO 2014/004113    1/2014

OTHER PUBLICATIONS

U.S. Appl. No. 13/657,553, filed Oct. 22, 2012.

(Continued)

*Primary Examiner* — Katherine M Shi
*Assistant Examiner* — Michael Mendoza
(74) *Attorney, Agent, or Firm* — Frost Brown Todd LLC

(57) ABSTRACT

An apparatus for operating on tissue comprises an end effector, a shaft assembly, and an interface assembly. The end effector comprises an ultrasonic blade. The shaft assembly includes an articulation section operable to deflect the end effector away from the longitudinal axis. The interface assembly is operable to drive the end effector. The interface assembly comprises a base and a plurality of drive shafts. The base is configured to couple with a dock of a robotic control system. The drive shafts are oriented perpendicular to the longitudinal axis of the shaft assembly. A first drive shaft may be operable to rotate the shaft assembly relative to the base. A second drive shaft may be operable to drive the articulation section. A third drive shaft may be operable to drive a clamping arm to pivot toward the ultrasonic blade.

17 Claims, 18 Drawing Sheets

(56) References Cited

U.S. PATENT DOCUMENTS

| | | | |
|---|---|---|---|
| 6,090,120 A | 7/2000 | Wright et al. |
| 6,231,565 B1 | 5/2001 | Tovey et al. |
| 6,325,811 B1 | 12/2001 | Messerly |
| 6,364,888 B1 | 4/2002 | Niemeyer et al. |
| 6,454,782 B1 | 9/2002 | Schwemberger |
| 6,500,176 B1 | 12/2002 | Truckai et al. |
| 6,589,200 B1 | 7/2003 | Schwemberger et al. |
| 6,752,815 B2 | 6/2004 | Beaupre |
| 6,783,524 B2 | 8/2004 | Anderson et al. |
| 6,855,123 B2 | 2/2005 | Nita |
| 7,112,201 B2 | 9/2006 | Truckai et al. |
| 7,125,409 B2 | 10/2006 | Truckai et al. |
| 7,135,030 B2 | 11/2006 | Schwemberger et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckal et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,455,208 B2 | 11/2008 | Wales et al. |
| 7,506,790 B2 | 3/2009 | Shelton, IV et al. |
| 7,524,320 B2 | 4/2009 | Tierney et al. |
| 7,549,564 B2 | 6/2009 | Boudreaux |
| 7,559,450 B2 | 7/2009 | Wales et al. |
| 7,621,930 B2 | 11/2009 | Houser |
| 7,654,431 B2 | 2/2010 | Hueil et al. |
| 7,691,098 B2 | 4/2010 | Wallace et al. |
| 7,780,054 B2 | 8/2010 | Wales |
| 7,784,662 B2 | 8/2010 | Wales et al. |
| 7,798,386 B2 | 9/2010 | Schall et al. |
| 7,808,891 B2 | 10/2010 | Nowlin et al. |
| 7,824,401 B2 | 11/2010 | Manzo et al. |
| 8,461,744 B2 | 6/2013 | Wiener et al. |
| 8,479,969 B2 | 7/2013 | Shelton, IV et al. |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,616,431 B2 | 12/2013 | Timm et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2010/0069940 A1 | 3/2010 | Miller et al. |
| 2011/0087212 A1 | 4/2011 | Aldridge et al. |
| 2011/0087218 A1 | 4/2011 | Boudreaux et al. |
| 2011/0295242 A1 | 12/2011 | Spivey et al. |
| 2011/0295269 A1* | 12/2011 | Swensgard et al. ........... 606/130 |
| 2012/0078243 A1 | 3/2012 | Worrell et al. |
| 2012/0078247 A1 | 3/2012 | Worrell et al. |
| 2012/0116379 A1 | 5/2012 | Yates et al. |
| 2012/0138660 A1 | 6/2012 | Shelton, IV et al. |
| 2012/0199630 A1 | 8/2012 | Shelton, IV et al. |
| 2012/0199632 A1 | 8/2012 | Spivey et al. |
| 2012/0203247 A1 | 8/2012 | Shelton, IV et al. |
| 2013/0012957 A1 | 1/2013 | Shelton, IV et al. |
| 2013/0023868 A1 | 1/2013 | Worrell et al. |
| 2013/0030428 A1 | 1/2013 | Worrell et al. |
| 2013/0267969 A1 | 10/2013 | Martin et al. |
| 2014/0005701 A1 | 1/2014 | Olson et al. |
| 2014/0005703 A1 | 1/2014 | Stulen et al. |
| 2014/0114334 A1 | 4/2014 | Olson et al. |
| 2015/0080924 A1 | 3/2015 | Stulen et al. |

OTHER PUBLICATIONS

U.S. Appl. No. 61/410,603, filed Nov. 5, 2010.
U.S. Appl. No. 61/597,603, filed Feb. 10, 2012.
International Search Report and Written Opinion dated Apr. 15, 2014 for Application No. PCT/US2014/016871.

* cited by examiner

ROBOTIC ULTRASONIC SURGICAL DEVICE WITH ARTICULATING END EFFECTOR

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. Examples of such ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744, on Jun. 11, 2013, the disclosure of which is incorporated by reference herein, U.S. patent application Ser. No. 13/538,588, filed Jun. 29, 2012, entitled "Surgical Instruments with Articulating Shafts," published as U.S. Pub. No., 2014/0005701 on Jan. 2, 2014, the disclosure of which is incorporated by reference herein; and U.S. patent application Ser. No. 13/657,553, filed Oct. 22, 2012, entitled "Flexible Harmonic Waveguides/Blades for Surgical Instruments," published as U.S. Pub. No. 2014/0114334 on Apr. 24, 2014, now U.S. Pat. No. 9,095,367issued on Aug. 4, 2015; the disclosure of which is incorporated by reference herein. Additionally, some of the foregoing surgical tools may include a cordless transducer such as that disclosed in and U.S. Pat. App. No. 61/410,603, filed Nov. 5, 2010, entitled "Energy-Based Surgical Instruments," the disclosure of which is incorporated by reference herein.

In addition, a variety of surgical instruments include a shaft having an articulation section, providing enhanced positioning capabilities for an end effector that is located distal to the articulation section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

Some surgical systems provide robotic control of a surgical instrument. With minimally invasive robotic surgery, surgical operations may be performed through a small incision in the patient's body. A robotic surgical system may be used with various types of surgical instruments, including but not limited to surgical staplers, ultrasonic instruments, electrosurgical instruments, and/or various other kinds of instruments, as will be described in greater detail below. An example of a robotic surgical system is the DAVINCI™ system by Intuitive Surgical, Inc., of Sunnyvale, Calif. By way of further example, one or more aspects of robotic surgical systems are disclosed in the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; and U.S. Pat. No. 7,824,401, entitled "Surgical Tool With Writed Monopolar Electrosurgical End Effectors," issued Nov. 2, 2010, the disclosure of which is incorporated by reference herein.

Additional examples of instruments that may be incorporated with a robotic surgical system are described in U.S. Pub. No. 2013/0012957, entitled "Automated End Effector Component Reloading System for Use with a Robotic System," published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 20, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, the disclosure of which is incorporated by reference herein; U.S. Pub. No. 2012/0203247, entitled "Robotically-Controlled Surgical End Effector System," published Aug. 9, 2012, issued as U.S. Pat. No. 8,753,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013, the disclosure of which is incorporated by reference herein; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein; U.S. patent application Ser. No. 13/443,101, entitled "Control Interface for Laparoscopic Suturing Instrument," filed Apr. 10, 2012, published as U.S. Pub. No. 2013/0267969 on Oct. 10, 2013, the disclosure of which is incorporated by reference herein; and U.S. Provisional Pat. App. No. 61/597,603, entitled "Robotically Controlled Surgical Instrument," filed Feb. 10, 2012, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
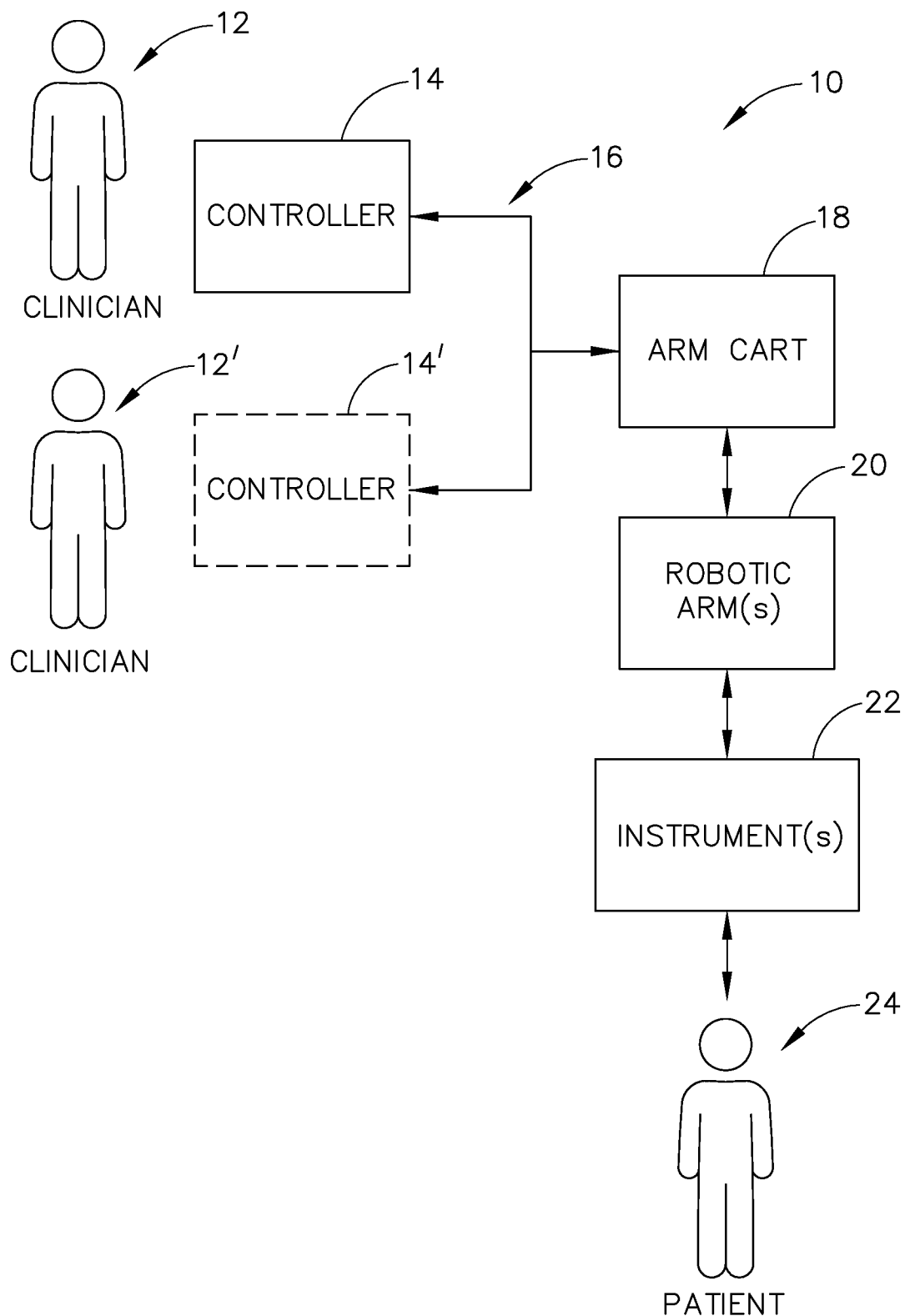
FIG. 1 depicts a block diagram of an exemplary robotic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a robotic surgical driver comprising a proximal housing having an interface that mechanically and electrically couples with a surgical instrument having a distal surgical end effector. The term "proximal" refers the position of an element closer to the robotic surgical driver housing and the term "distal" refers to the position of an element closer to the surgical end effector of the surgical instrument and further away from the housing.

I. Exemplary Robotic Surgical System Overview

FIG. 1 illustrates an exemplary robotic surgical system (10). System (10) comprises at least one controller (14) and at least one arm cart (18). Arm cart (18) is mechanically and/or electrically coupled to one or more robotic manipulators or arms (20). Each robotic arm (20) comprises one or more surgical instruments (22) for performing various surgical tasks on a patient (24). Operation of arm cart (18), including arms (20) and instruments (22), may be directed by a clinician (12) from controller (14). In some examples, a second controller (14'), operated by a second clinician (12'), may also direct operation of the arm cart (18) in conjunction with the first clinician (12'). For example, each of the clinicians (12, 12') may control different arms (20) of the cart or, in some cases, complete control of arm cart (18) may be passed between the clinicians (12, 12'). In some examples, additional arm carts (not shown) may be utilized on the patient (24). These additional arm carts may be controlled by one or more of the controllers (14, 14').

Arm cart(s) (18) and controllers (14, 14') may be in communication with one another via a communications link (16), which may be any suitable type of wired and/or wireless communications link carrying any suitable type of signal (e.g., electrical, optical, infrared, etc.) according to any suitable communications protocol. Communications link (16) may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network.

Figure 2:
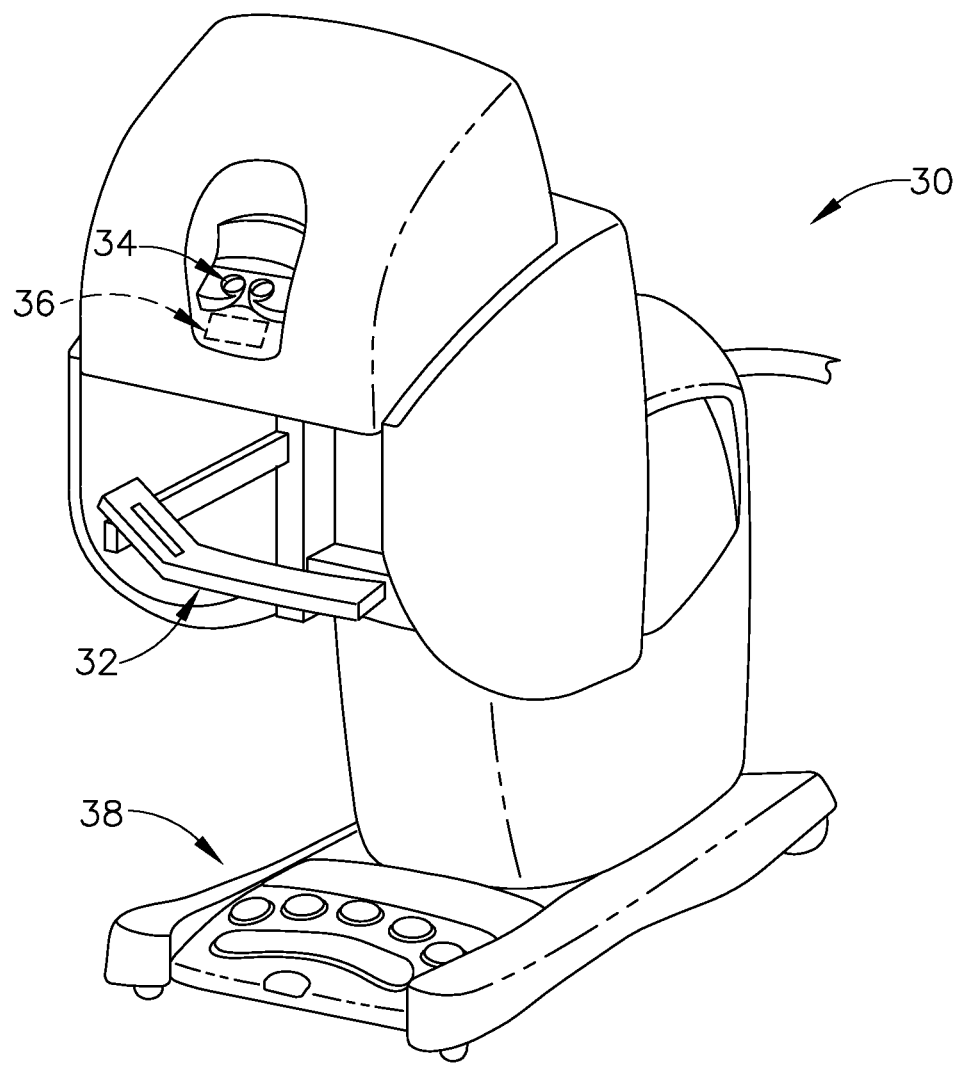
FIG. 2 depicts a perspective view of an exemplary controller of the system of FIG. 1.

FIG. 2 shows an exemplary controller (30) that may serve as a controller (14) of system (10). In this example, controller (30) generally includes user input assembly (32) having precision user input features (not shown) that are grasped by the surgeon and manipulated in space while the surgeon views the surgical procedure via a stereo display (34). The user input features of user input assembly (32) may include manual input devices that move with multiple degrees of freedom; and that include an actuatable handle for intuitively actuating tools (e.g., for closing grasping saws, applying an electrical potential to an electrode, etc). Controller (30) of the present example also includes an array of footswitches (38) providing additional control of arms (20) and instruments (22) to the surgeon. Display (34) may show views from one or more endoscopes viewing the surgical site within the patient and/or any other suitable view(s). In addition, a feedback meter (36) may be viewed through the display (34) and provide the surgeon with a visual indication of the amount of force being applied to a component of instrument (22) (e.g., a cutting member or clamping member, etc.). Other sensor arrangements may be employed to provide controller (30) with an indication as to whether a staple cartridge has been loaded into an end effector of instrument (22), whether an anvil of instrument (22) has been moved to a closed position prior to firing, and/or some other operational condition of instrument (22).

Figure 3:
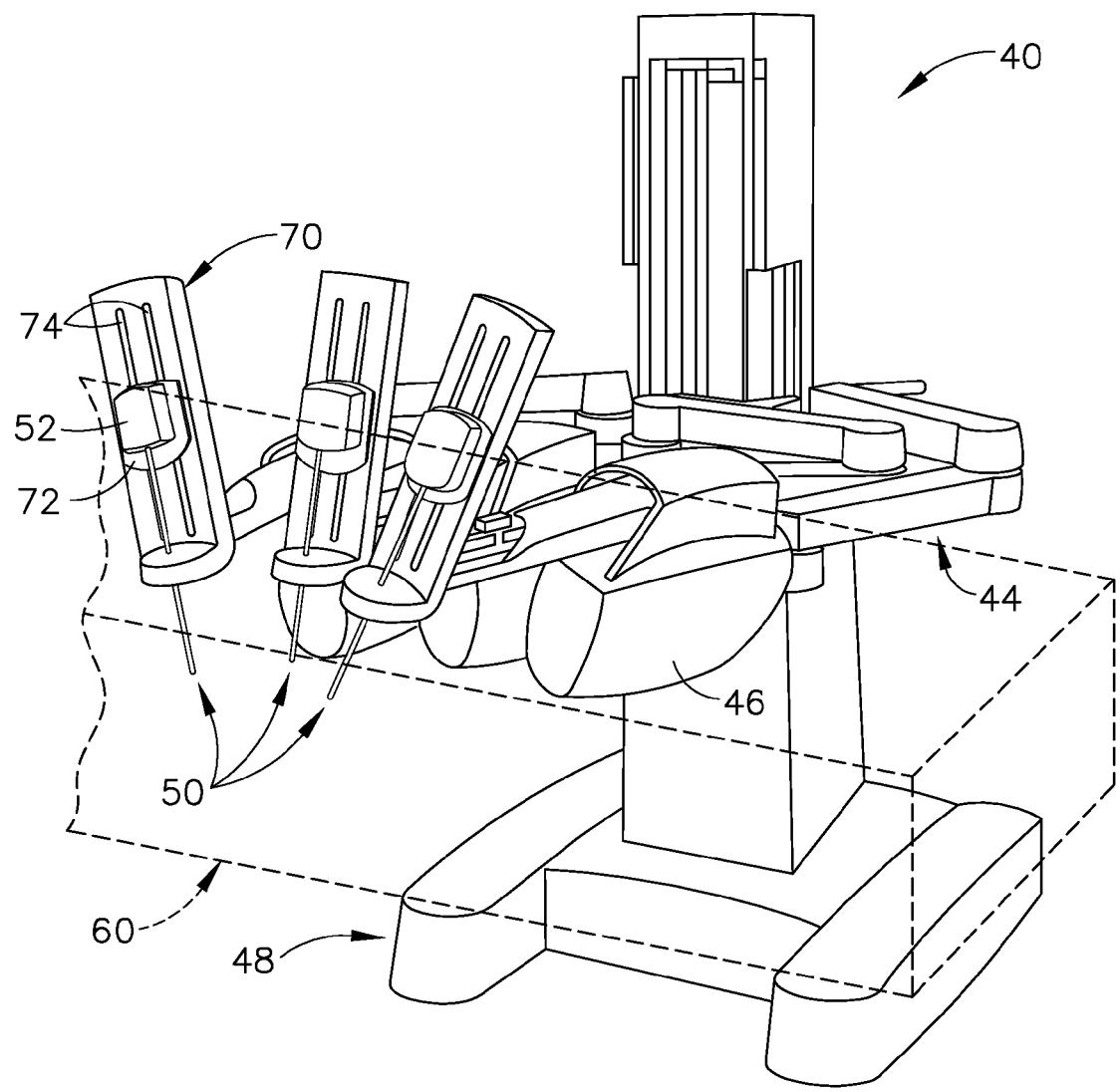
FIG. 3 depicts a perspective view of an exemplary robotic arm cart of the system of FIG. 1.
Figure 4:
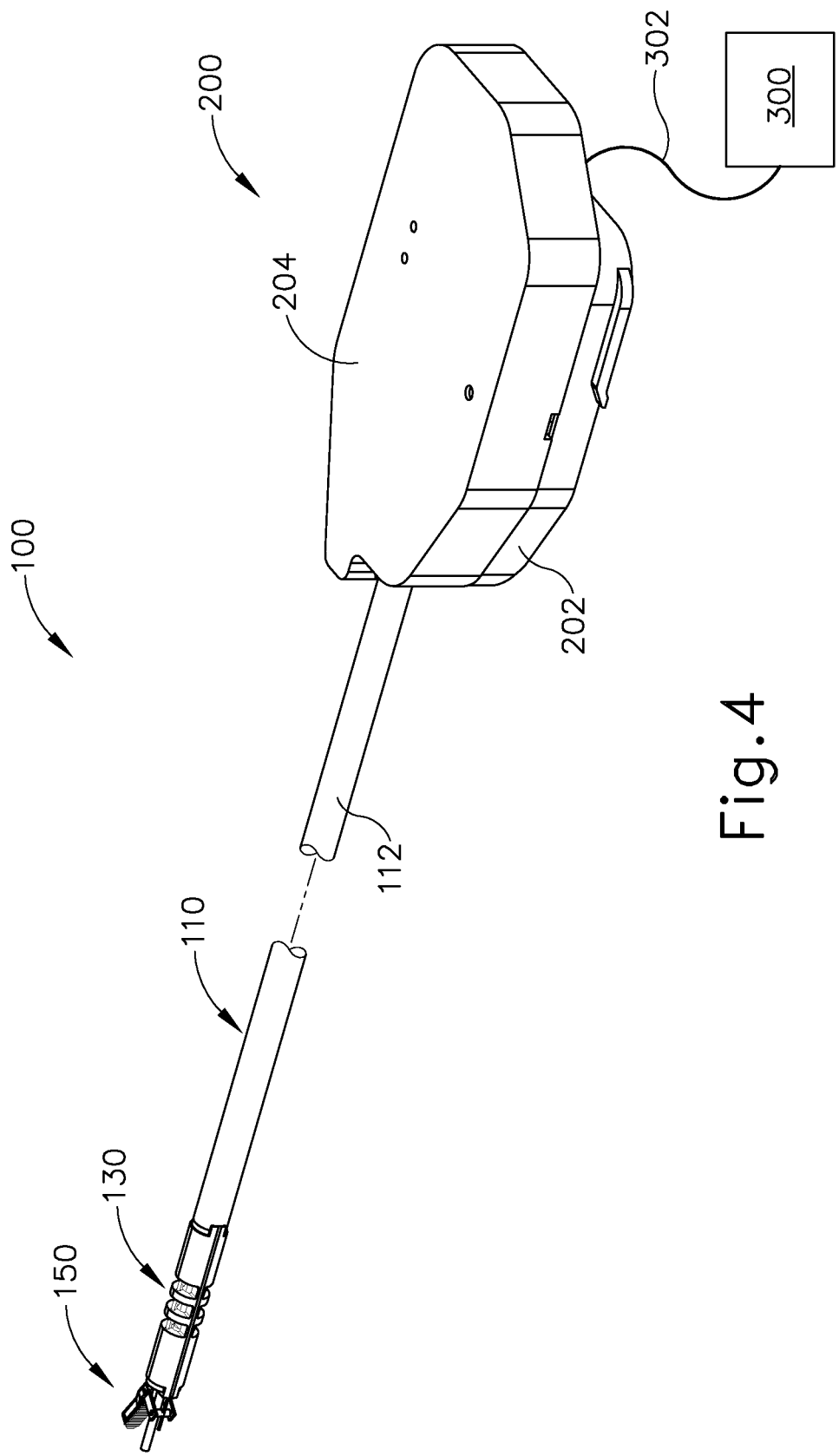
FIG. 4 depicts a perspective view of an exemplary surgical instrument suitable for incorporation with the system of FIG. 1.

FIG. 3 shows an exemplary robotic arm cart (40) that may serve as of arm cart (18) of system (10). In this example, arm cart (40) is operable to actuate a plurality of surgical instruments (50). While three instruments (50) are shown in this example, it should be understood that arm cart (40) may be operable to support and actuate any suitable number of surgical instruments (50). Surgical instruments (50) are each supported by a series of manually articulatable linkages, generally referred to as set-up joints (44), and a robotic manipulator (46). These structures are herein illustrated with protective covers extending over much of the robotic linkage. These protective covers may be optional, and may be limited in size or entirely eliminated in some versions to minimize the inertia that is encountered by the servo mechanisms used to manipulate such devices, to limit the volume of moving components so as to avoid collisions, and to limit the overall weight of cart (40).

Each robotic manipulator (46) terminates at an instrument platform (70), which is pivotable, rotatable, and otherwise movable by manipulator (46). Each platform includes an instrument dock (72) that is slidable along a pair of tracks (74) to further position instrument (50). Such sliding is motorized in the present example. Each instrument dock (72) includes mechanical and electrical interfaces that couple with an interface assembly (52) of instrument (50). By way of example only, dock (72) may include four rotary outputs that couple with complementary rotary inputs of interface assembly (52). Such rotary drive features may drive various functionalities in instrument (50), such as is described in various references cited herein and/or as is described in greater detail below. Electrical interfaces may establish communication via physical contact, inductive coupling, and/or otherwise; and may be operable to provide electrical power to one or more features in instrument (50), provide commands and/or data communication to instrument (50), and/or provide commands and/or data communication from instrument (50). Various suitable ways in which an instrument dock (72) may mechanically and electrically communicate with an interface assembly (52) of an instrument (50) will be apparent to those of ordinary skill in the art in view of the teachings herein. It should also be understood that instrument (50) may include one or more cables that couple with a separate power source and/or control unit, to provide communication of power and/or commands/data to/from instrument (50).

Arm cart (40) of the present example also includes a base (48) that is movable (e.g., by a single attendant) to selectively position arm cart (40) in relation to a patient. Cart (40) may generally have dimensions suitable for transporting the cart (40) between operating rooms. Cart (40) may be configured to fit through standard operating room doors and onto standard hospital elevators. In some versions, an automated instrument reloading system (not shown) may also be positioned in or near the work envelope (60) of arm cart (40), to selectively reload components (e.g., staple cartridges, etc.) of instruments (50).

In addition to the foregoing, it should be understood that one or more aspects of system (10) may be constructed in accordance with at least some of the teachings of U.S. Pat. No. 5,792,135; U.S. Pat. No. 5,817,084; U.S. Pat. No. 5,878, 193; U.S. Pat. No. 6,231,565; U.S. Pat. No. 6,783,524; U.S. Pat. No. 6,364,888; U.S. Pat. No. 7,524,320; U.S. Pat. No. 7,691,098; U.S. Pat. No. 7,806,891; U.S. Pat. No. 7,824,401; and/or U.S. Pub. No. 2013/0012957, issued as U.S. Pat. No. 8,844,789 on Sep. 30, 2014. The disclosures of each of the foregoing U.S. Patents and U.S. Patent Publication are incorporated by reference herein. Still other suitable features and operabilities that may be incorporated into system (10) will be apparent to those of ordinary skill in the art in view of the teachings herein.

II. Exemplary Ultrasonic Surgical Instrument with Articulation Feature

FIGS. 4-18 show an exemplary ultrasonic surgical instrument (100) that may be used as at least one instrument (50) within system (10). At least part of instrument (100) may be constructed and operable in accordance with at least some of the teachings of U.S. Pat. No. 5,322,055; U.S. Pat. No. 5,873, 873; U.S. Pat. No. 5,980,510; U.S. Pat. No. 6,325,811; U.S. Pat. No. 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, now U.S. Pat. No. 9,023,071, issued on May 5, 2015; U.S. Pub. No. 2011/0015660, issued as U.S. Pat. No. 8,461,744 on Jun. 11, 2013; U.S. patent application Ser. No. 13/538,588, published as U.S. Pub. No. 2014/0005701 on Jan. 2, 2014; U.S. patent application Ser. No. 13/657,553, published as U.S. Pub. No. 2014/0114334 on Apr. 24, 2014, now U.S. Pat. No. 9,095,367, issued on Aug. 4, 2015; and/or U.S. Pat. App. No. 61/410,603. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. In other words, instrument (100) operates similar to an endocutter type of stapler, except that instrument (100) provides tissue welding through application of ultrasonic vibrational energy instead of providing lines of staples to join tissue. This same ultrasonic vibrational energy also separates tissue similar to severing of tissue by a translating knife member. It should also be understood that instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (100) of the present example includes an interface assembly (200), a shaft assembly (110), an articulation section (130), and an end effector (150). Interface assembly (200) is configured to couple with a dock (72) of robotic arm cart (40) and is thereby further operable to drive articulation section (130) and end effector (150) as will be described in greater detail below. As will also be described in greater detail below, instrument (100) is operable to articulate end effector (150) to provide a desired positioning relative to tissue (e.g., a large blood vessel, etc.), then apply ultrasonic vibrational energy to the tissue with end effector (150) to thereby cut and seal the tissue.

As will be described in greater detail below, instrument (100) of the present example includes an ultrasonic transducer (120), which is operable to convert electrical power into ultrasonic vibrations. In some instances, transducer (120) receives power directly through dock (72). In some other instances, transducer (120) includes a separate cable (302) that directly couples transducer (120) with a generator (300). Such a generator (300) may include a power source and control module that is configured to provide a power profile to transducer (120) that is particularly suited for the generation of ultrasonic vibrations through transducer (120). By way of example only, generator (300) may comprise a GEN 300 sold by Ethicon Endo-Surgery, Inc. of Cincinnati, Ohio. In addition or in the alternative, generator (300) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. Still other suitable forms that generator (300) may take, as well as various features and operabilities that generator (300) may provide, will be apparent to those of ordinary skill in the art in view of the teachings herein. It should also be understood that at least part of the functionality of generator (300) may be incorporated directly into interface assembly (200). By way of example only, interface assembly (200) may include an integral battery or other integral power source, as well as any circuitry needed to condition power from a battery or other integral power source to drive ultrasonic transducer (120).

A. Exemplary End Effector and Acoustic Drivetrain

Figure 6:
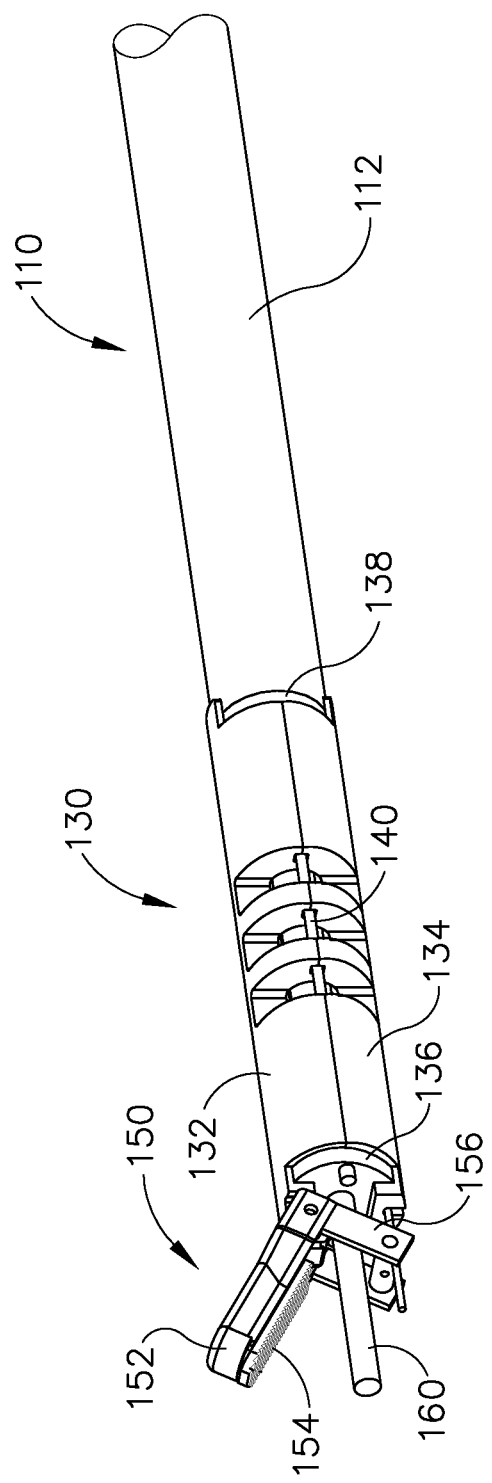
FIG. 6 depicts a perspective view of the end effector and shaft assembly articulation section of the instrument of FIG. 4.
Figure 7:
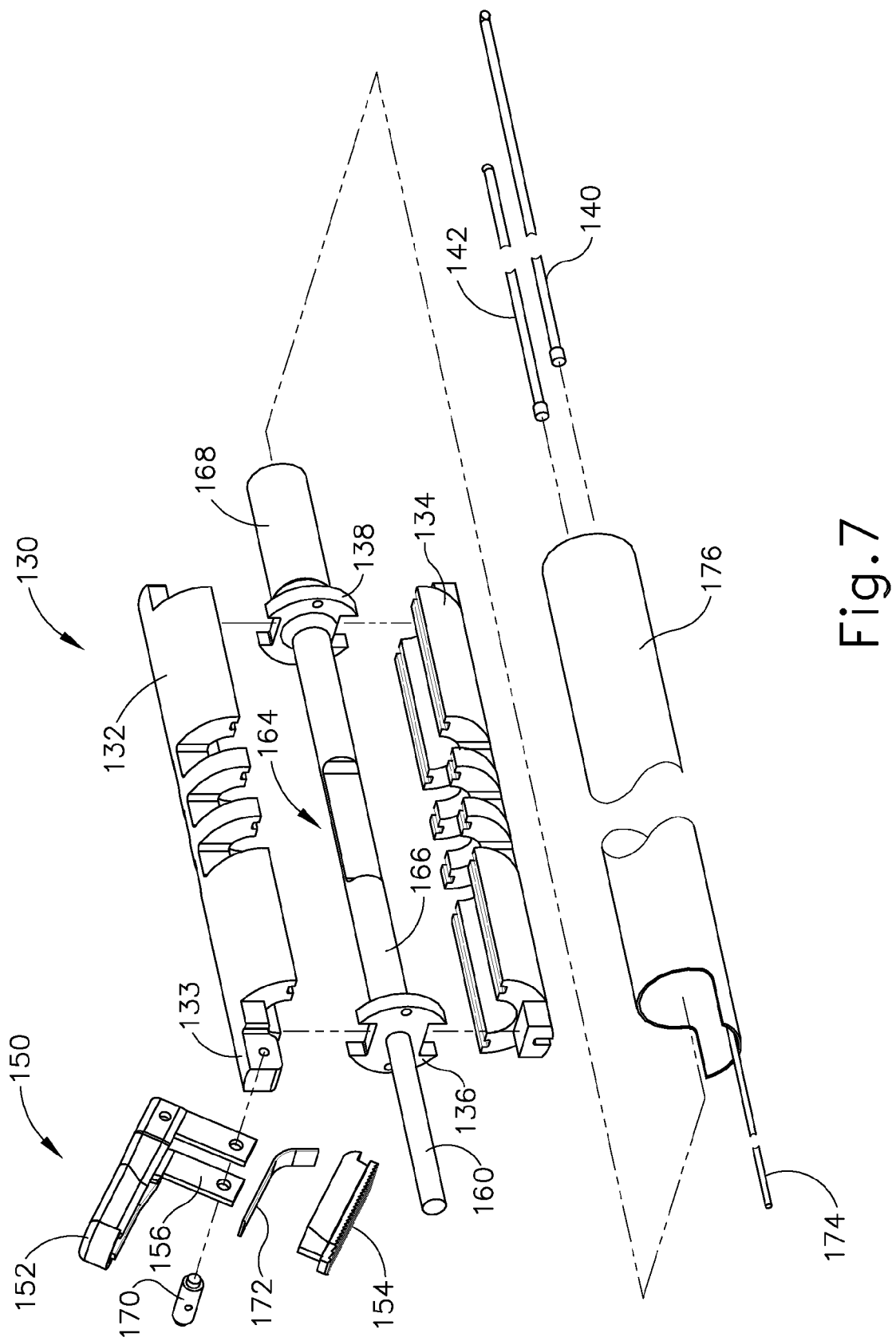
FIG. 7 depicts an exploded view of the end effector and articulation section of FIG. 6.
Figure 8:
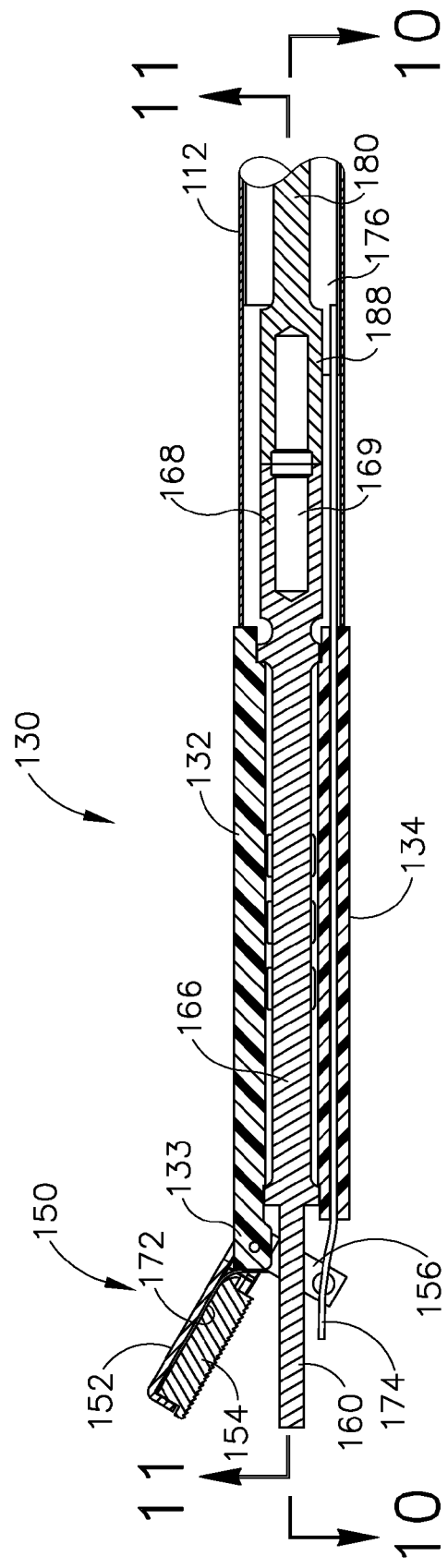
FIG. 8 depicts a lateral cross-sectional view of the end effector and articulation section of FIG. 6.
Figure 9:
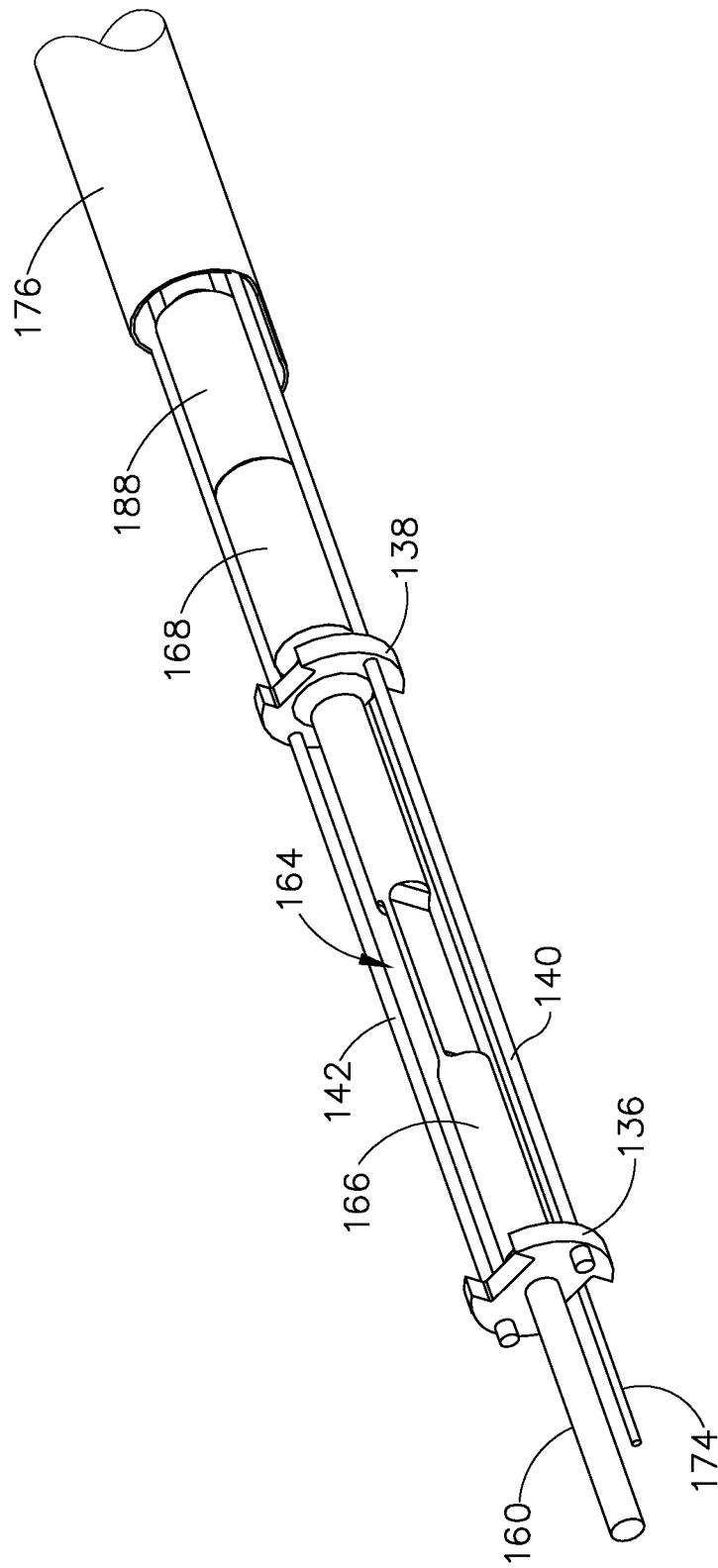
FIG. 9 depicts a perspective view of the end effector and articulation section of FIG. 6, with an outer sheath omitted and with clamp pad features omitted.
Figure 10:
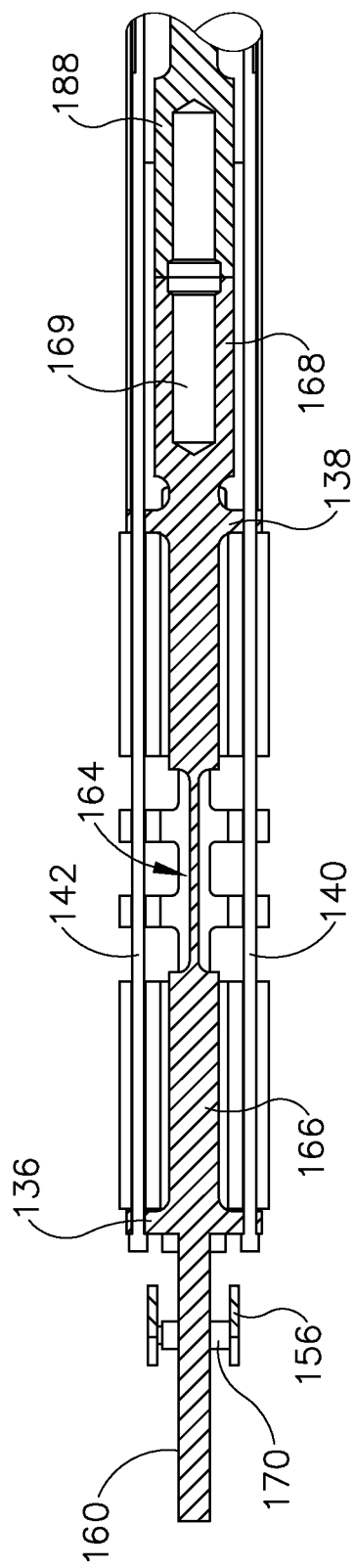
FIG. 10 depicts a cross-sectional view of the end effector and articulation section of FIG. 6, taken along line 10-10 of FIG. 8.
Figure 11:
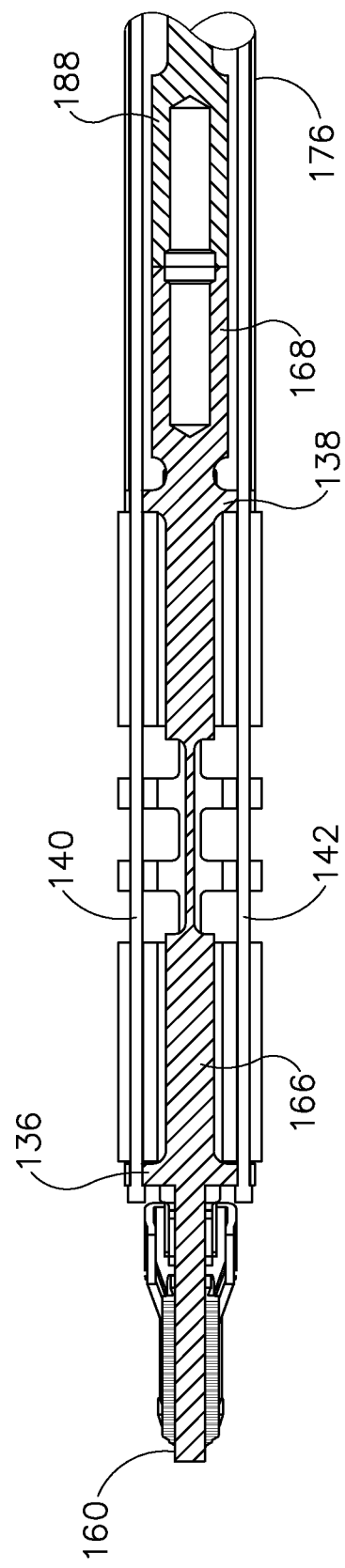
FIG. 11 depicts a cross-sectional view of the end effector and articulation section of FIG. 6, taken along line 11-11 of FIG. 8.
Figure 12:
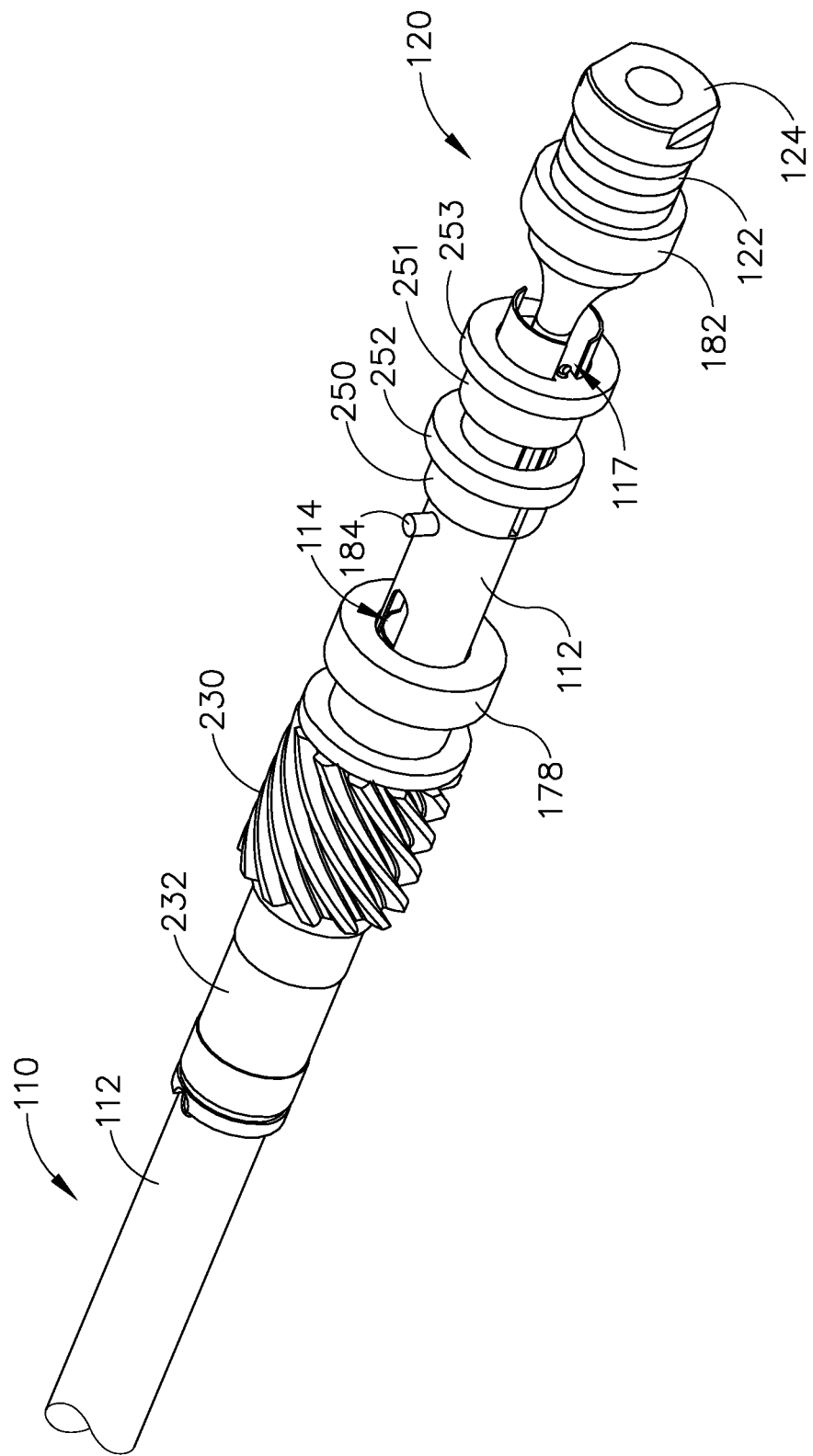
FIG. 12 depicts a perspective view of the proximal end of the shaft assembly of the instrument of FIG. 4.

As best seen in FIGS. 6-8, end effector (150) of the present example comprises a clamp arm (152) and an ultrasonic blade (160). Clamp arm (152) includes a clamp pad (154) that is secured to the underside of clamp arm (152), facing blade (160). Clamp arm (152) is pivotally secured to a distally projecting tongue (133) of a first ribbed body portion (132), which forms part of articulation section (130) as will be described in greater detail below. Clamp arm (152) is operable to selectively pivot toward and away from blade (160) to selectively clamp tissue between clamp arm (152) and blade (160). A pair of arms (156) extend transversely to clamp arm (152) and are secured to a pin (170) that extends laterally between arms (156). A rod (174) is secured to pin (170). Rod (174) extends distally from a closure tube (176) and is unitarily secured to closure tube (176).

Figure 13:
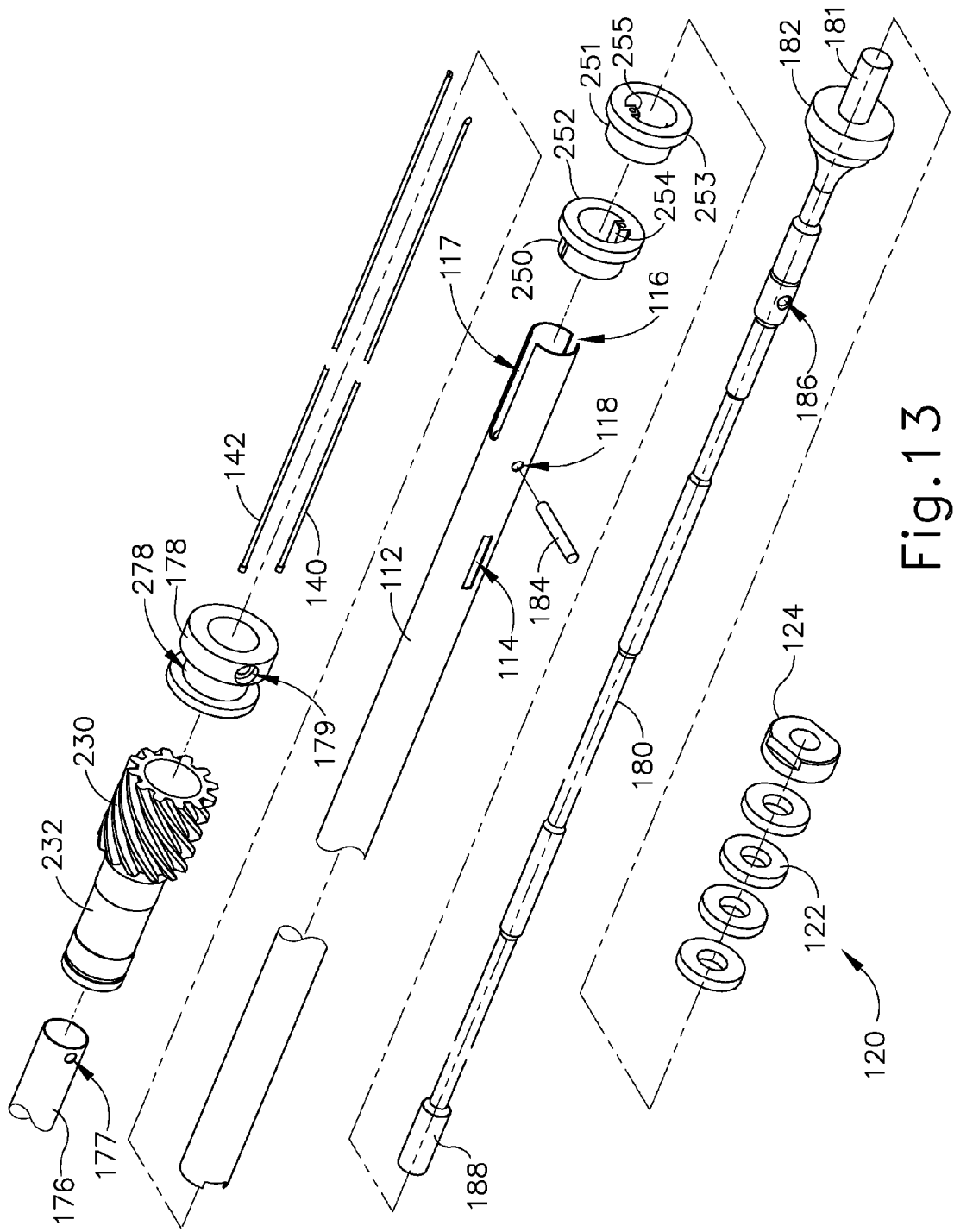
FIG. 13 depicts an exploded view of the proximal end of the shaft assembly of the instrument of FIG. 4.

A driving ring (178) is secured to the proximal end of closure tube (176). In particular, and as best seen in FIG. 13, the proximal end of closure tube (176) includes a transverse opening (177) that is configured to align with a transverse opening (179) of driving ring (178). These openings (177, 179) are configured to receive a set screw (not shown) or other feature that secures driving ring (178) to closure tube (176). Driving ring (178) is slidably and coaxially disposed about the exterior of outer sheath (112); while closure tube (176) is slidably and coaxially disposed within the interior of outer sheath (112). However, outer sheath (112) includes a longitudinally extending slot (114) that is configured to receive the set screw that secures driving ring (178) to closure tube (176). Thus, slot (114) allows driving ring (178) and closure tube (176) to translate together relative to outer sheath (112). The positioning of the set screw in slot (114) also provides rotation of closure tube (176) and driving ring (178) about the longitudinal axis of outer sheath (112) when outer sheath (112) is rotated about its longitudinal axis as described in greater detail below.

As will also be described in greater detail below, interface assembly (200) includes features that are operable to drive driving ring (178), closure tube (176), and rod (174) longitudinally relative to outer sheath (112) and relative to articulation section (130). It should be understood that this translation of driving ring (178), closure tube (176), and rod (174) will provide pivoting of clamp arm (152) toward blade (160) (when ring (178), tube (176), and rod (174) are translated proximally); or away from blade (160) (when ring (178), tube (176), and rod (174) are translated distally). Rod (174) is sufficiently flexible to bend with articulation section (130). However, rod (174) has sufficient tensile and compressive strength to drive clamp arm (152) when rod (174) is translated, regardless of whether articulation section (130) is in a straight or bent configuration.

As best seen in FIGS. 7-8 leaf spring (172) is captured between clamp arm (152) and clamp pad (172) and abuts the distal face of tongue (133). Leaf spring (172) is resiliently biased to drive clamp arm (152) away from blade (160) to the open position shown in FIGS. 4, 6, and 8. Leaf spring (172) thus further biases tube (176) and rod (174) distally. Of course, like other components described herein, leaf spring (172) may be omitted if desired. Furthermore, clamp arm (152) and clamp pad (154) may be omitted if desired.

Figure 17:
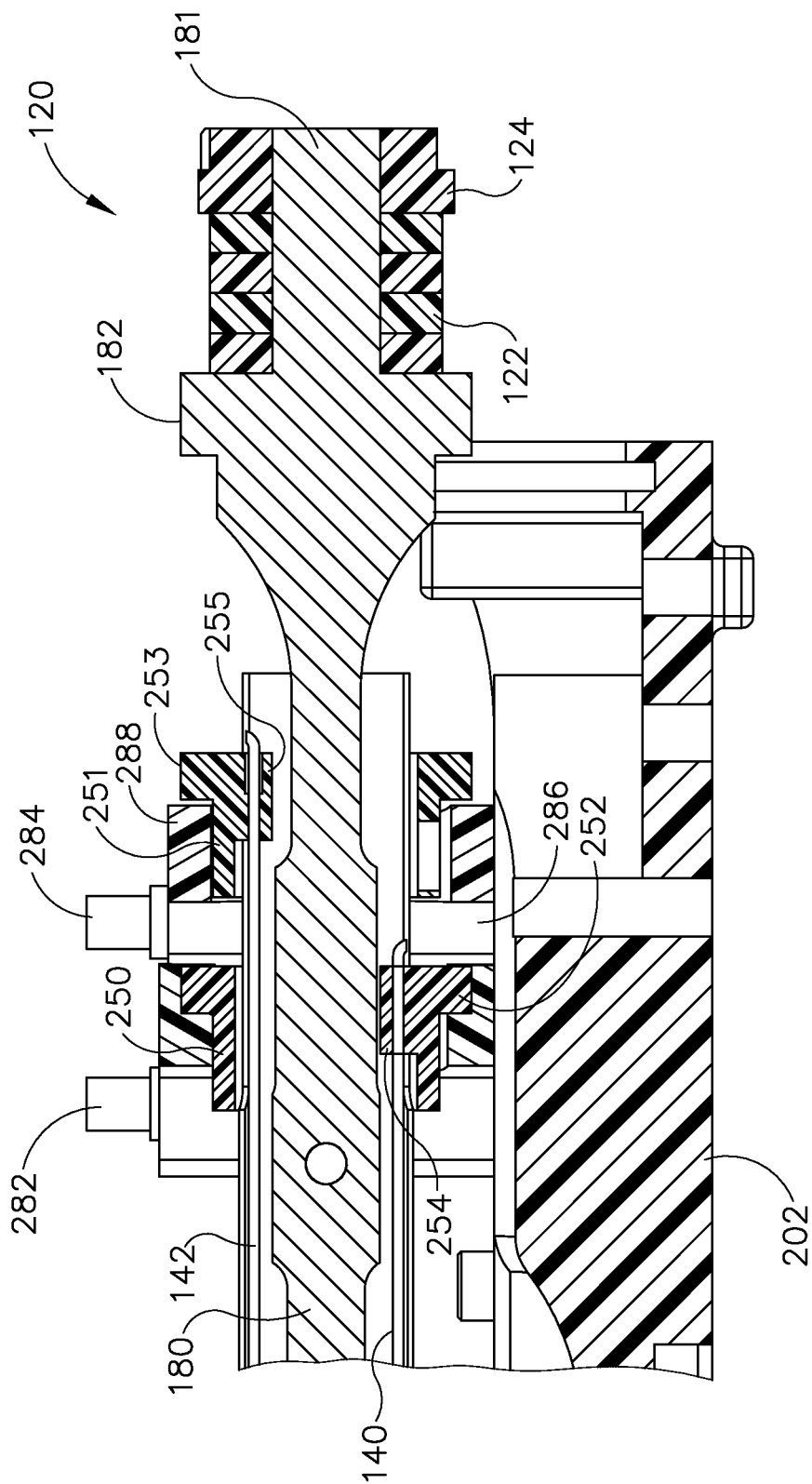
FIG. 17 depicts a lateral cross-sectional view of a proximal portion of the proximal end of the instrument of FIG. 4, taken along line 17-17 of FIG. 15.
Figure 18:
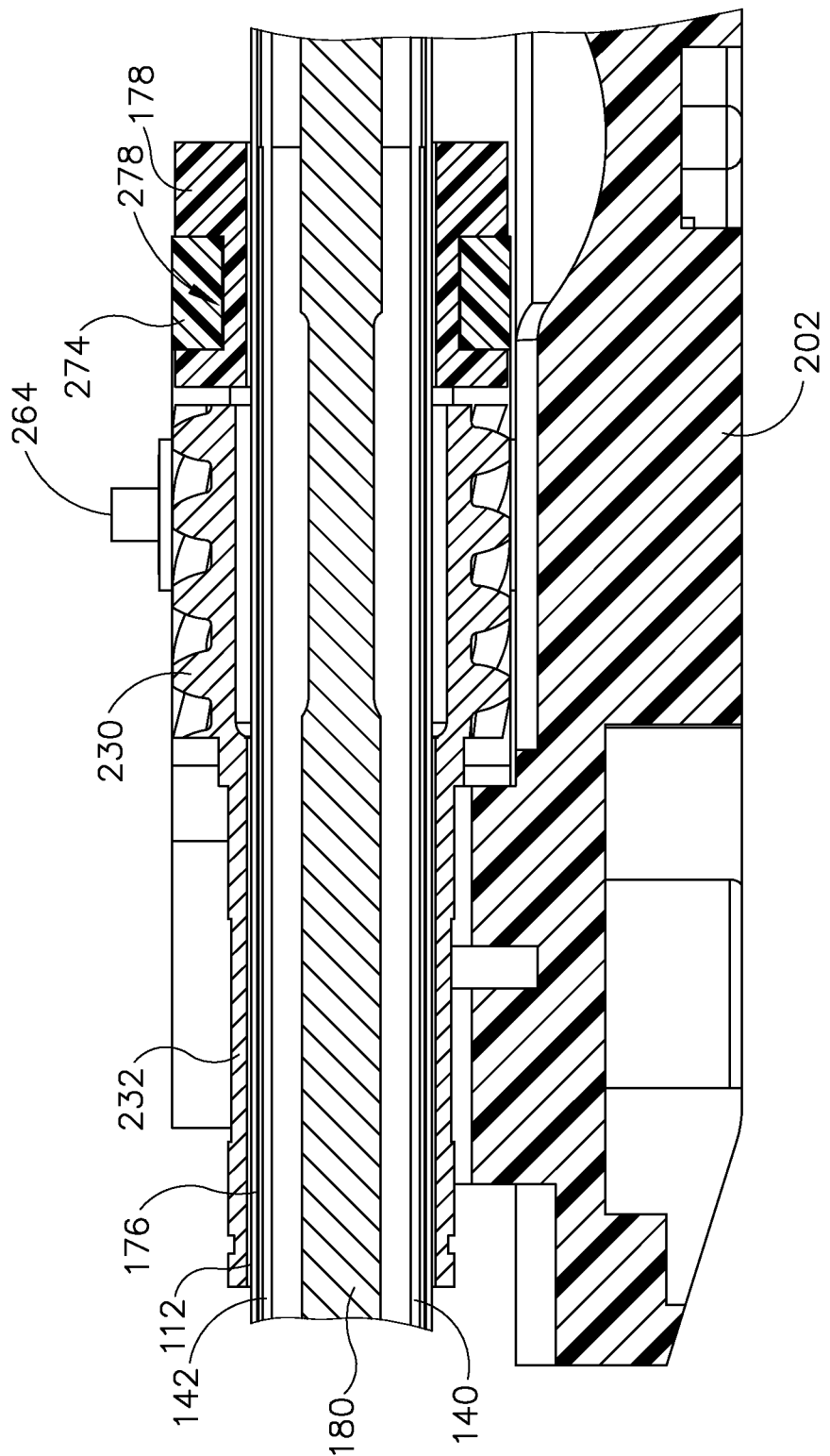
FIG. 18 depicts a lateral cross-sectional view of a distal portion of the proximal end of the instrument of FIG. 4, taken along line 18-18 of FIG. 15.

Blade (160) of the present example is operable to vibrate at ultrasonic frequencies in order to effectively cut through and seal tissue, particularly when the tissue is being clamped between clamp pad (154) and blade (160). Blade (160) is positioned at the distal end of an acoustic drivetrain. This acoustic drivetrain includes a transducer assembly (120), a rigid acoustic waveguide (180), and a flexible acoustic waveguide (166). As best seen in FIGS. 5 and 12-17, transducer assembly (120) includes a set of piezoelectric discs (122) located proximal to a horn (182) of rigid acoustic waveguide (180). Piezoelectric discs (122) are coaxially positioned along a proximally extending bolt (181), which is a unitary feature of acoustic waveguide (180) located proximal to horn (182). An endmass nut (124) is secured to bolt (181), thereby securing piezoelectric discs (122) to rigid acoustic waveguide (180). As noted above, piezoelectric discs (122) are operable to convert electrical power into ultrasonic vibrations, which are then transmitted along rigid acoustic waveguide (180) to blade (160). Rigid acoustic waveguide (180) is best seen in FIGS. 13 and 17-18. As shown in FIG. 13, rigid acoustic waveguide (180) includes a transverse opening (186) that complements a transverse opening (118) formed in outer sheath (118). A pin (184) is disposed in openings (118, 186) to couple outer sheath (112) with rigid acoustic waveguide (180). This coupling provides rotation of acoustic waveguide (180) (and the rest of the acoustic drivetrain) about the longitudinal axis of outer sheath (112) when outer sheath (112) is rotated about its longitudinal axis as will be described in greater detail below. In the present example, opening (186) is located at a position corresponding to a node associated with resonant ultrasonic vibrations communicated through rigid acoustic waveguide (180).

Rigid acoustic waveguide (180) distally terminates in a coupling (188), which can be seen in FIGS. 8-11 and 13. Coupling (188) is secured to coupling (168) by a double-threaded bolt (169). Coupling (168) is located at the proximal end of flexible acoustic waveguide (166). As best seen in FIGS. 7-11, flexible acoustic waveguide (166) includes a distal flange (136), a proximal flange (138), and a narrowed section (164) located between flanges (138). In the present example, flanges (136, 138) are located at positions corresponding to nodes associated with resonant ultrasonic vibrations communicated through flexible acoustic waveguide (166). Narrowed section (164) is configured to allow flexible acoustic waveguide (166) to flex without significantly affecting the ability of flexible acoustic waveguide (166) to transmit ultrasonic vibrations. By way of example only, narrowed section (164) may be configured in accordance with one or more teachings of U.S. patent application Ser. No. 13/538,588, published as U.S. Pub. No. 2014/0005701 on Jan. 2, 2014 and/or U.S. patent application Ser. No. 13/657,553, published as U.S. Pub. No. 2014/0114334 on Apr. 24, 2014, now U.S. Pat. No. 9,095,367, issued on Aug. 4, 2015, the disclosures of which are incorporated by reference herein. It should be understood that either waveguide (166, 180) may be configured to amplify mechanical vibrations transmitted through waveguide (166, 180). Furthermore, either waveguide (166, 180) may include features operable to control the gain of the longitudinal vibrations along waveguide (166, 180) and/or features to tune waveguide (166, 180) to the resonant frequency of the system.

In the present example, the distal end of blade (160) is located at a position corresponding to an anti-node associated with resonant ultrasonic vibrations communicated through flexible acoustic waveguide (166), in order to tune the acoustic assembly to a preferred resonant frequency $f_o$ when the acoustic assembly is not loaded by tissue. When transducer assembly (120) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (120) of the present example is activated, these mechanical oscillations are transmitted through waveguides (180, 166) to reach blade (160), thereby providing oscillation of blade (160) at the resonant ultrasonic frequency. Thus, when tissue is secured between blade (160) and clamp pad (154), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (154) to also cauterize the tissue. While some configurations for an acoustic transmission assembly and transducer assembly (120) have been described, still other suitable configurations for an acoustic transmission assembly and transducer assembly (120) will be apparent to one or ordinary skill in the art in view of the teachings herein. Similarly, other suitable configurations for end effector (150) will be apparent to those of ordinary skill in the art in view of the teachings herein.

B. Exemplary Shaft Assembly and Articulation Section

Shaft assembly (110) of the present example extends distally from interface assembly (200). Articulation section (130) is located at the distal end of shaft assembly (110), with end effector (150) being located distal to articulation section (130). Shaft assembly (110) includes an outer sheath (112) that encloses drive features and the above-described acoustic transmission features that couple interface assembly (200) with articulation section (130) and end effector (150). Shaft assembly (110) is rotatable about the longitudinal axis defined by sheath (112), relative to interface assembly (200). Such rotation may provide rotation of end effector (150), articulation section (130), and shaft assembly (110) unitarily. Of course, rotatable features may simply be omitted if desired.

Articulation section (130) is operable to selectively position end effector (150) at various lateral deflection angles relative to the longitudinal axis defined by sheath (112). Articulation section (130) may take a variety of forms. By way of example only, articulation section (130) may be configured in accordance with one or more teachings of U.S. Pub. No. 2012/0078247, the disclosure of which is incorporated by reference herein. As another merely illustrative example, articulation section (130) may be configured in accordance with one or more teachings of U.S. patent application Ser. No. 13/538,588, published as U.S. Pub. No. 2014/0005701 on Jan. 2, 2014 and/or U.S. patent application Ser. No. 13/657,553, published as U.S. Pub. No. 2014/0114334 on Apr. 24, 2014, now U.S. Pat. No. 9,095,367, issued on Aug. 4, 2015, the disclosures of which are incorporated by reference herein. Various other suitable forms that articulation section (130) may take will be apparent to those of ordinary skill in the art in view of the teachings herein. It should also be understood that some versions of instrument (10) may simply lack articulation section (130).

As best seen in FIGS. 6-11 articulation section (130) of the present example comprises a first ribbed body portion (132) and a second ribbed body portion (134), with a pair of articulation bands (140, 142) extending through channels defined at the interfaces between ribbed body portions (132, 134). Ribbed body portions (132, 134) are substantially longitudinally positioned between flanges (136, 138) of flexible acoustic waveguide (166). The distal ends of articulation bands (140, 142) are unitarily secured to distal flange (136). Articulation bands (140, 142) also pass through proximal flange (138), yet articulation bands (140, 142) are slidable relative to proximal flange (138).

The proximal end of articulation band (140) is secured to a first drive ring (250); while the proximal end of articulation band (142) is secured to a second drive ring (251). As best seen in FIGS. 13 and 17, first drive ring (250) includes an annular flange (252) and an inwardly projecting anchor feature (254); while second drive ring (251) also includes an annular flange (253) and an inwardly projecting anchor feature (255). The proximal end of articulation band (140) is fixedly secured within anchor feature (254) while the proximal end of articulation band (142) is fixedly secured within anchor feature (255). Drive rings (250, 251) are slidably disposed about the proximal end of outer sheath (112). Outer sheath (112) includes a pair of longitudinally extending slots (116, 117) that are configured to respectively receive anchor features (254, 255). Slots (116, 117) allow drive rings (250, 251) to translate relative to outer sheath (112). The positioning of anchor features (254, 255) in slots (116, 117) also provides rotation of rings (250, 251) and articulation bands (140, 142) about the longitudinal axis of outer sheath (112) when outer sheath (112) is rotated about its longitudinal axis as described in greater detail below.

As will be described in greater detail below, interface assembly (200) is operable to selectively pull one articulation band (140, 142) proximally by pulling proximally on drive ring (250); while simultaneously allowing the other articulation band (140, 142) and drive ring (251) to translate distally. It should be understood that, as one articulation band (140, 142) is pulled proximally, this will cause articulation section (130) to bend, thereby laterally deflecting end effector (150) away from the longitudinal axis of shaft assembly (110) at an articulation angle. In particular, end effector (150) will be articulated toward the articulation band (140, 142) that is being pulled proximally. During such articulation, the other articulation band (140, 142) will be pulled distally by flange (136). Ribbed body portions (132, 134) and narrowed section (164) are all sufficiently flexible to accommodate the above-described articulation of end effector (150).

C. Exemplary Robotic Arm Interface Assembly

FIGS. 5 and 14-18 show interface assembly (200) of the present example in greater detail. As shown, interface assembly (200) comprises a base (202) and a housing (204). It should be noted that housing (204) is only shown in FIG. 4 and is omitted from FIGS. 5 and 14-18 for the sake of clarity. Housing (204) comprises a shell that simply encloses drive components. In some versions, housing (204) also includes an electronic circuit board, chip, and/or other feature that is configured to identify instrument (100).

Figure 5:
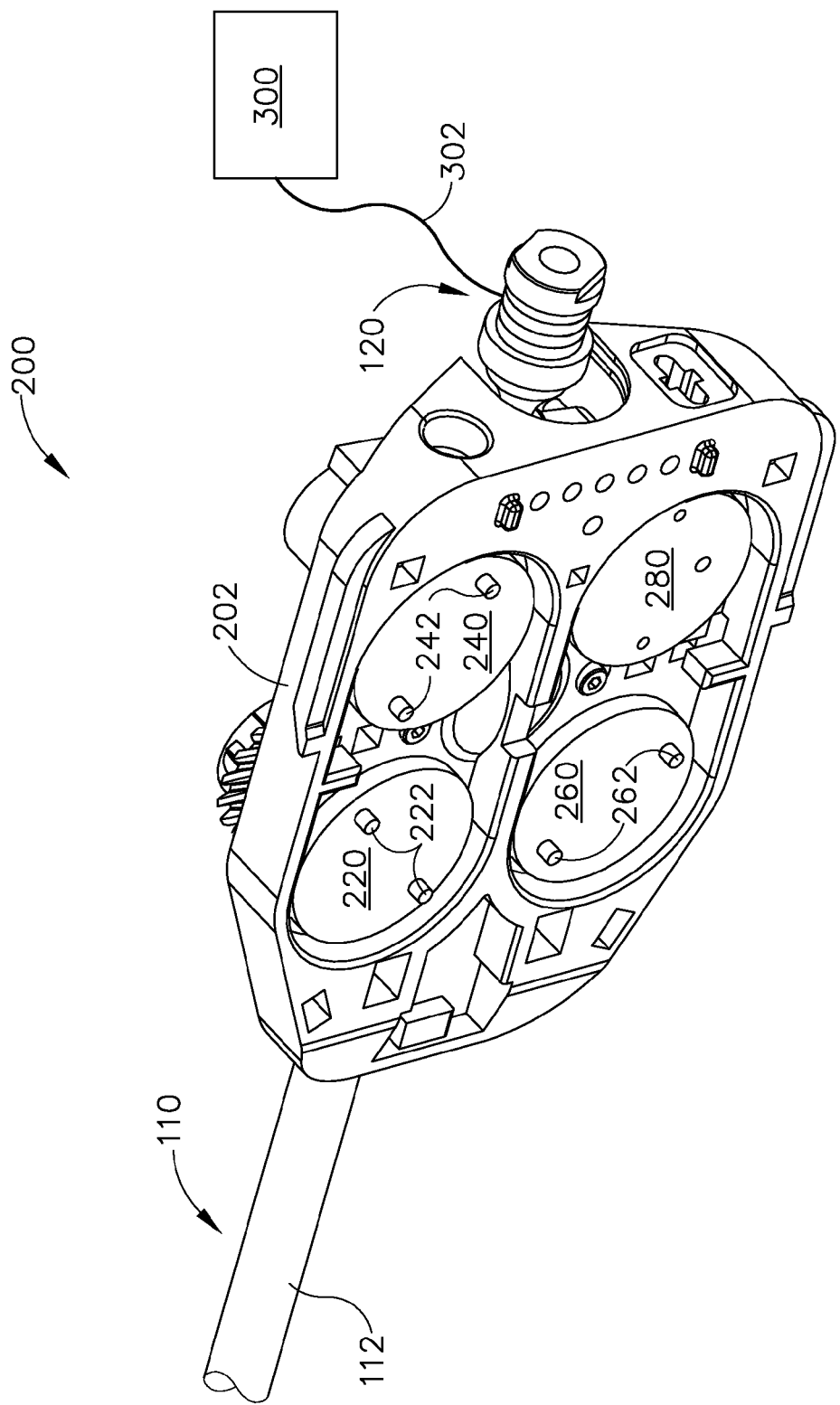
FIG. 5 depicts a perspective view of the underside of the base assembly of the instrument of FIG. 4.

Base (202) is configured to engage dock (72) of robotic arm cart (40). While not shown, it should be understood that base (202) may also include one or more electrical contacts and/or other features operable to establish electrical communication with a complementary feature of dock (72). A shaft support structure (206) extends upwardly from base (202) and provides support to shaft assembly (110) (while still allowing shaft assembly (110) to rotate). By way of example only, shaft support structure (206) may include a busing, bearings, and/or other features that facilitate rotation of shaft assembly (110) relative to support structure (206). As shown in FIG. 5, base (202) further includes three drive discs (220, 240, 260) that are rotatable relative to base (202). Each disc (220, 240, 260) includes a respective pair of unitary pins (222, 242, 262) that couple with complementary recesses (not shown) in drive elements of dock (72). In some versions, one pin (222, 242, 262) of each pair is closer to the axis of rotation of the corresponding disc (220, 240, 260), to ensure proper angular orientation of disc (220, 240, 260) relative to the corresponding drive element of dock (72).

Figure 14:
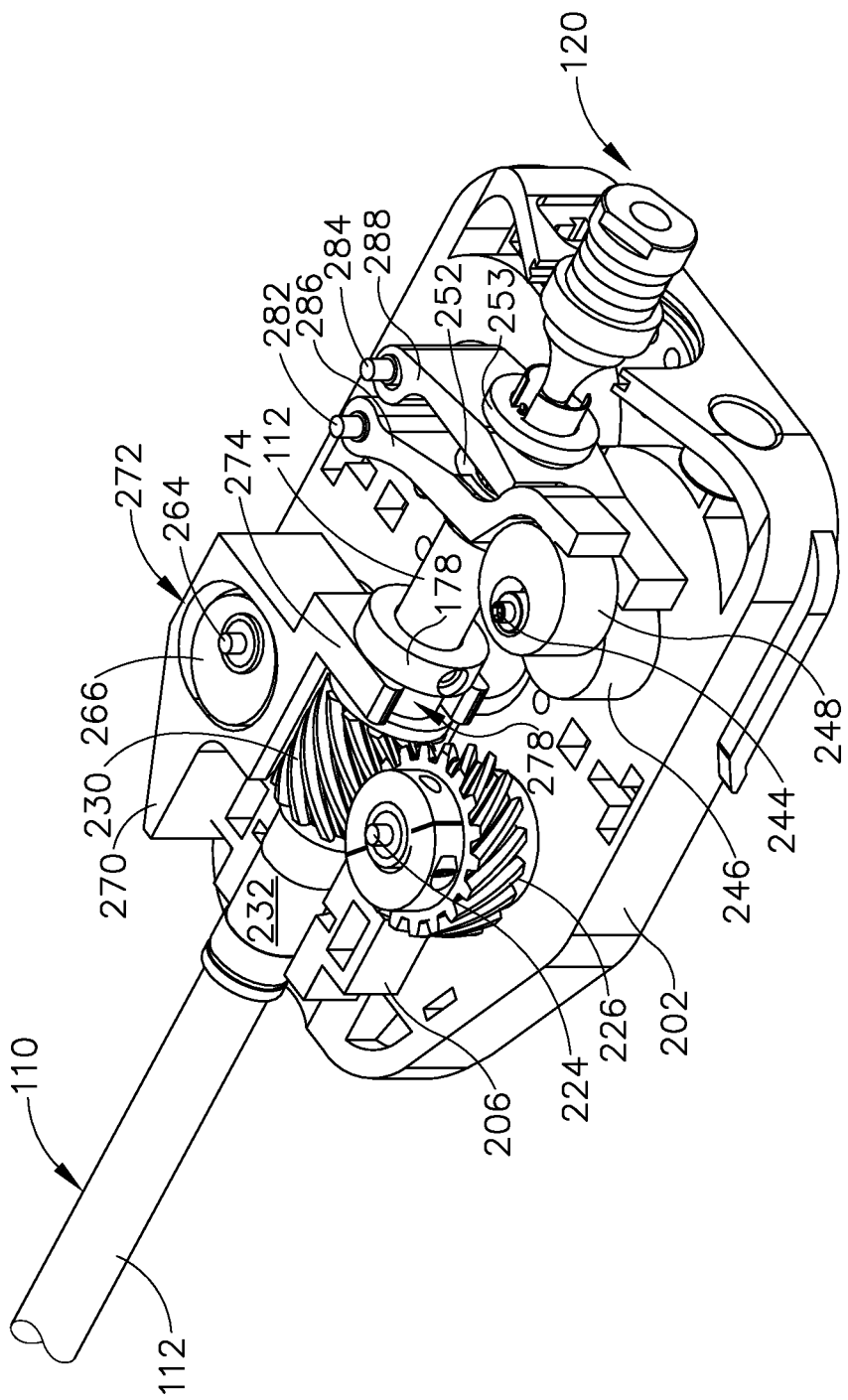
FIG. 14 depicts a perspective view of the proximal end of the instrument of FIG. 4, with the outer cover omitted.
Figure 15:
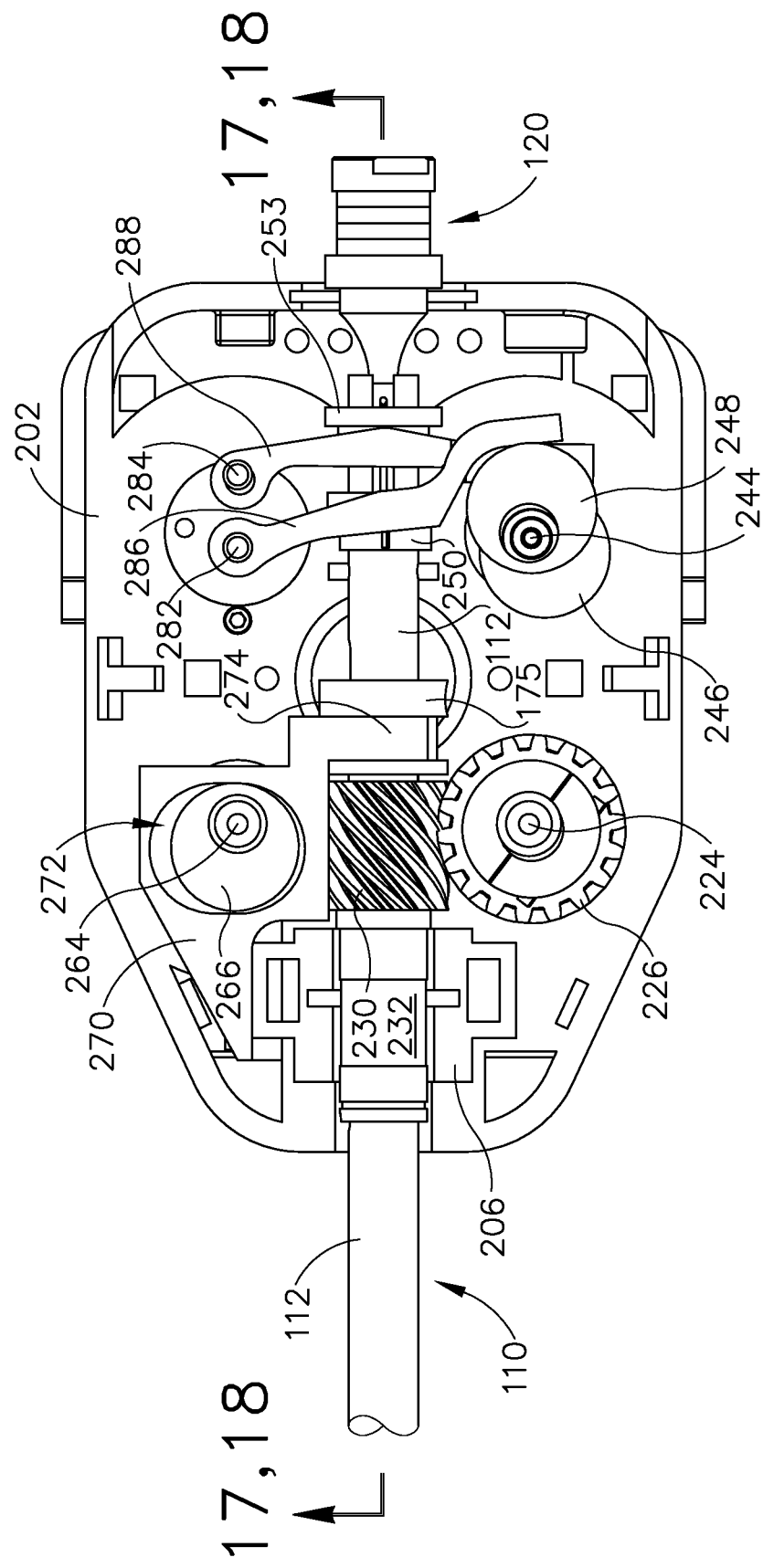
FIG. 15 depicts a top plan view of the proximal end of the instrument of FIG. 4, with the outer cover omitted.
Figure 16:
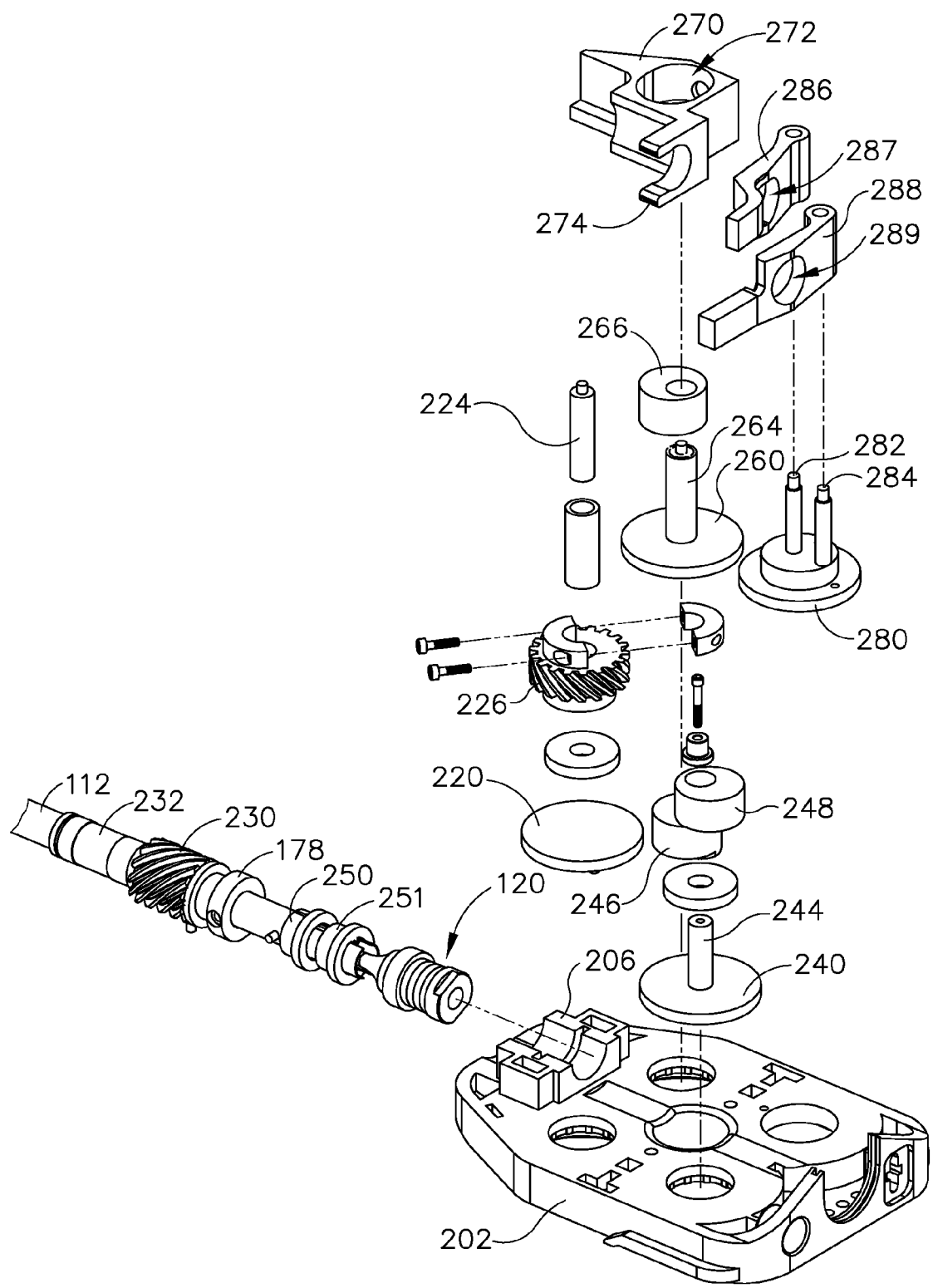
FIG. 16 depicts an exploded view of the proximal end of the instrument of FIG. 4, with the outer cover omitted.

As best seen in FIGS. 14-16, a drive shaft (224, 244, 264) extends unitarily upwardly from each disc (220, 240, 260). As will be described in greater detail below, discs (220, 240, 260) are independently operable to provide independent rotation of shaft assembly (110), bending of articulation section (130), and translation of closure tube (176), through independent rotation of drive shafts (224, 244, 264). Base (202) also includes an idle disc (280), which simply does not rotate or drive any components. A pair of fixed pivot pins (282, 284) extend unitarily upwardly from disc (280).

As best seen in FIGS. 14-16, a first helical gear (226) is fixedly secured to drive shaft (224), such that rotation of the corresponding disc (220) provides rotation of first helical gear (226). First helical gear (226) meshes with a second helical gear (230), which is unitarily secured to a sleeve (232). Sleeve (232) is unitarily secured to outer sheath (112). Thus, rotation of first helical gear (226) provides rotation of shaft assembly (110). It should be understood that rotation of first helical gear (226) about a first axis is converted into rotation of second helical gear (230) about a second axis, which is orthogonal to the first axis. A clockwise (CW) rotation of second helical gear (230) (viewed from the top down) results in CW rotation of shaft assembly (110) (viewed from the distal end of shaft assembly (110) toward the proximal end of shaft assembly (110)), depending on the thread orientation of helical gears (226, 230). A counter-clockwise (CCW) rotation of second helical gear (132) (viewed from the top down) results in CCW rotation of shaft assembly (110) (viewed from the distal end of shaft assembly (110) toward the proximal end of shaft assembly (110)), again depending on the thread orientation of helical gears (226, 230). It should therefore be understood that shaft assembly (110) may be actuated by rotating drive shaft (224). Other suitable ways in which shaft assembly (110) may be rotated will be apparent to those of ordinary skill in the art in view of the teachings herein.

As also best seen in FIGS. 14-16, a pair of cylindraceous cams (246, 248) are fixedly secured to drive shaft (244), such that rotation of the corresponding disc (240) provides rotation of cams (246, 248). Cams (246, 248) are both mounted eccentrically to drive shaft (244), such that the longitudinal axes of cams (246, 248) are offset from yet parallel to the longitudinal axis of drive shaft (244). In addition, cams (246, 248) are offset in an opposing manner, such that cams (246, 248) laterally protrude relative to drive shaft (244) in opposite directions. Cams (246, 248) are positioned to drive pivot arms (286, 288). Pivot arm (286) is pivotally coupled with pivot pin (282); while pivot arm (288) is pivotally coupled with pivot pin (284). First drive ring (250) passes through an opening (287) formed through first drive arm (286); while second drive ring (251) passes through an opening (289) formed through second drive arm (288). Flanges (252, 253) each have an outer diameter that is larger than the inner diameter of the corresponding opening (287, 289). Flanges (252, 253) thus restrict distal movement of rings (250, 251) relative to respective drive arms (286, 288).

As drive shaft (244) is rotated, one of cams (246, 248) will push proximally on the corresponding arm (286, 288), depending on the positioning of these components and the angular position of cams (246, 248) at the time of rotation. In some instances, cam (246) will drive arm (288) proximally, such that arm (288) pivots CCW (viewed from the top down) about pin (284). Arm (288) will bear against flange (253) during such pivoting, thereby pulling ring (251) and articulation band (142) proximally. This proximal movement of articulation band (142) will cause articulation section (130) to bend, with end effector (150) being deflected toward band (142). This bending of articulation section (130) will pull articulation band (140) distally, which will in turn pull ring (250) and its flange (252) distally. The distal motion of flange (252) will drive arm (286) distally, such that arm (286) pivots CW (viewed from the top down) about pin (282). Cam (248) will be oriented to permit such distal pivoting of arm (286). As drive shaft (244) continues to rotate (or if drive shaft (244) is rotated in the opposite direction), the above pushing and pulling will eventually be reversed. In other words, cam (248) may drive arm (286) proximally while cam (246) permits arm (288) to pivot distally during bending of articulation section (130) to provide deflection of end effector (150) toward band (140). It should therefore be understood that articulation section (130) may be actuated by rotating drive shaft (244). Other suitable ways in which articulation section (130) may be actuated will be apparent to those of ordinary skill in the art in view of the teachings herein.

As also best seen in FIGS. 14-16, a cylindraceous cam (266) is fixedly secured to drive shaft (264), such that rotation of the corresponding disc (260) provides rotation of cam (266). Cam (266) is mounted eccentrically to drive shaft (264), such that the longitudinal axis of cam (266) is offset from yet parallel to the longitudinal axis of drive shaft (264). Cam (266) is disposed in an oblong opening (272) formed through a rack (270), which is translatable relative to base (202). Rack (270) includes a laterally extending fork (274). Fork (274) is disposed in an annular recess (278) of driving ring (178), which is secured to closure tube (176) as noted above. The configuration of cam (266) and the configuration of recess (272) provide a relationship whereby rack (270) translates longitudinally in response to rotation of drive shaft (264) and cam (266). This translation of rack (270) provides translation of closure tube (176) due to the engagement between fork (274) and driving ring (178); and the engagement between driving ring (178) and closure tube (176). It should therefore be understood that clamp arm (152) may be selectively driven away from or toward blade (160) by rotating drive shaft (264). Other suitable ways in which clamp arm (152) may be actuated will be apparent to those of ordinary skill in the art in view of the teachings herein.

D. Exemplary Operation

In an exemplary use, arm cart (40) is used to insert end effector (150) into a patient via a trocar. Articulation section (130) is substantially straight, and clamp arm (152) is pivoted toward blade (160), when end effector (150) and part of shaft assembly (110) are inserted through the trocar. Drive shaft (224) may be rotated through drive features in dock (72) that are coupled with the corresponding disc (220), to position end effector (150) at a desired angular orientation relative to the tissue. Drive shaft (244) may then be rotated through drive features in dock (72) that are coupled with the corresponding disc (240), to pivot or flex articulation section (130) of shaft assembly (110) in order to position end effector (150) at a desired position and orientation relative to an anatomical structure within the patient. Drive shaft (264) may then be rotated through drive features in dock (72) that are coupled with the corresponding disc (260), to pivot clamp arm (152) away from blade (160), thereby effectively opening end effector (150).

Tissue of the anatomical structure is then captured between clamp pad (154) and blade (160) by rotating drive shaft (264) to advance closure tube (176) distally, by actuating drive features in dock (72) that are coupled with the corresponding disc (260). In some instances, this involves clamping two layers of tissue forming part of a natural lumen defining anatomical structure (e.g., blood vessel, portion of gastrointestinal tract, portion of reproductive system, etc.) in a patient; though it should be understood that instrument (100) may be used on various kinds of tissues and anatomical locations. With tissue captured between clamp pad (154) and blade (160), transducer (120) is activated to provide ultrasonic vibrations at blade (160). This simultaneously severs the tissue and denatures proteins in adjacent tissue cells, thereby providing a coagulative effect with relatively little thermal spread.

The above operation of shaft assembly (110), articulation section (130), and end effector (150) may be repeated as many times as desired in various locations within the patient. When the operator wishes to withdraw end effector (150) from the patient, drive shaft (244) may be rotated through drive features in dock (72) that are coupled with the corresponding disc (240), to straighten articulation section (130). Drive shaft (264) may be rotated through drive features in dock (72) that are coupled with the corresponding disc (260), to pivot clamp arm (152) toward blade (160), thereby effectively closing end effector (150). Arm cart (40) is then used to withdraw end effector (150) from the patient and trocar. Other suitable ways in which instrument (100) may be operable and operated will be apparent to those of ordinary skill in the art in view of the teachings herein.

III. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc.

In versions where the teachings herein are applied to an electrosurgical instrument, it should be understood that the teachings herein may be readily applied to an ENSEAL® Tissue Sealing Device by Ethicon Endo-Surgery, Inc., of Cincinnati, Ohio. In addition or in the alternative, it should be understood that the teachings herein may be readily combined with the teachings of one or more of the following: U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued on Oct. 20, 2015, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued on Jul. 28, 2015, the disclosure of which is incorporated by reference herein; and/or U.S. Pub. No. 2013/0023868, entitled "Surgical Instrument with Contained Dual Helix Actuator Assembly," published Jan. 31, 2013, the disclosure of which is incorporated by reference herein. Other suitable ways in which the teachings herein may be applied to an electrosurgical instrument will be apparent to those of ordinary skill in the art in view of the teachings herein.

In versions where the teachings herein are applied to a surgical stapling instrument, it should be understood that the teachings herein may be combined with the teachings of one or more of the following, the disclosures of all of which are incorporated by reference herein: U.S. Pat. No. 7,380,696; U.S. Pat. No. 7,404,508; U.S. Pat. No. 7,455,208; U.S. Pat. No. 7,506,790; U.S. Pat. No. 7,549,564; U.S. Pat. No. 7,559,450; U.S. Pat. No. 7,654,431; U.S. Pat. No. 7,780,054; U.S. Pat. No. 7,784,662; and/or U.S. Pat. No. 7,798,386. Other suitable ways in which the teachings herein may be applied to a surgical stapling instrument will be apparent to those of ordinary skill in the art in view of the teachings herein.

It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) an end effector, wherein the end effector comprises an ultrasonic blade;
   (b) a shaft assembly, wherein the end effector is disposed at a distal end of the shaft assembly, wherein the shaft assembly defines a longitudinal axis, wherein the shaft assembly includes an articulation section operable to deflect the end effector away from the longitudinal axis; and
   (c) an interface assembly, wherein the interface assembly is configured to drive the end effector, wherein the interface assembly comprises:
      (i) a base, wherein the base is configured to couple with a dock of a robotic control system,
      (ii) at least one eccentric cam,
      (iii) a plurality of drive shafts, wherein at least one of the drive shafts is operably coupled to the at least one eccentric cam to thereby rotate the at least one eccentric cam, wherein rotation of the at least one eccentric cam is operable to drive the articulation section, and
      (iv) a plurality of drive discs associated with the plurality of drive shafts, wherein the drive discs each comprise a respective pair of pins, wherein the pins are configured to couple with complementary drive features of a robotic control system.

2. An apparatus for operating on tissue, the apparatus comprising:
   (a) an end effector, wherein the end effector comprises an ultrasonic blade;
   (b) a shaft assembly, wherein the end effector is disposed at a distal end of the shaft assembly, wherein the shaft assembly defines a longitudinal axis, wherein the shaft assembly includes an articulation section operable to deflect the end effector away from the longitudinal axis;
   (c) an interface assembly, wherein the interface assembly is configured to drive the end effector, wherein the interface assembly comprises:
      (i) a base,
      (ii) at least one eccentric cam operably coupled to the articulation section, and
      (iii) a plurality of drive shafts, wherein the drive shafts are rotatable relative to the base, wherein at least one of the drive shafts is operably coupled to the at least one eccentric cam to thereby rotate the at least one eccentric cam; and
   (d) a robotic control system, wherein the robotic control system comprises:
      (i) a robotic arm including a dock, wherein the base is configured to couple with the dock, wherein the dock includes drive features operable to couple with the drive shafts, and
      (ii) a user interface assembly, wherein the user interface assembly is operable to remotely control the drive features.

3. The apparatus of claim 2,
   wherein the shaft assembly comprises an acoustic waveguide assembly, wherein the waveguide assembly comprises:
      (i) a rigid waveguide portion, and
      (ii) a flexible waveguide portion, wherein the flexible waveguide portion extends through the articulation section, wherein the flexible waveguide portion includes a narrowed section positioned proximal to the end effector and configured to provide flexing of the flexible waveguide portion,
   wherein waveguide assembly is operable to transmit ultrasonic vibrations to the ultrasonic blade.

4. The apparatus of claim 2, wherein the shaft assembly is rotatable relative to the interface assembly.

5. The apparatus of claim 4, wherein a first drive shaft of the plurality of drive shafts is rotatable to rotate the shaft assembly relative to the interface assembly.

6. The apparatus of claim 5, wherein the shaft assembly and the first drive shaft include meshing helical gears.

7. The apparatus of claim 2, wherein the end effector further comprises a clamp arm, wherein the clamp arm is operable to pivot relative to the ultrasonic blade.

8. The apparatus of claim 7, wherein a first drive shaft of the plurality of drive shafts is rotatable to pivot the clamp arm toward the ultrasonic blade.

9. The apparatus of claim 8, wherein the shaft assembly comprises a translating member coupled between the first drive shaft and the clamp arm.

10. The apparatus of claim 9, wherein the interface assembly further comprises:
    (i) an eccentric cam secured to the first drive shaft, and
    (ii) a rack coupled with the translating member, wherein the eccentric cam is operable to drive the rack proximally in response to rotation of the first drive shaft, to thereby pivot the clamp arm toward the ultrasonic blade.

11. The apparatus of claim 2, wherein the articulation section comprises a first articulation band, wherein the first articulation band is translatable relative to the shaft assembly to deflect the end effector away from the longitudinal axis.

12. The apparatus of claim 11, wherein the articulation section further comprises a second articulation band, wherein the first articulation band is translatable relative to the shaft assembly to deflect the end effector away from the longitudinal axis in a first direction, wherein the second articulation band is translatable relative to the shaft assembly to deflect the end effector away from the longitudinal axis in a second direction.

13. The apparatus of claim 11, wherein a first drive shaft of the plurality of drive shafts is rotatable to translate the first articulation band.

14. The apparatus of claim 13, wherein the interface assembly further comprises:
   (i) an eccentric cam secured to the first drive shaft, and
   (ii) a pivoting arm coupled with the first articulation band, wherein the eccentric cam is operable to drive the pivoting arm proximally in response to rotation of the first drive shaft, to thereby deflect the end effector away from the longitudinal axis.

15. The apparatus of claim 11, wherein the articulation section comprises a pair of ribbed bodies, wherein the first articulation band is apposed between the pair of ribbed bodies.

16. The apparatus of claim 2, wherein the base comprises a plurality of drive discs, wherein the drive discs are operable to rotate the drive shafts.

17. The apparatus of claim 16, wherein the drive discs each comprise a respective pair of pins, wherein the pins are configured to couple with complementary drive features of a robotic control system.

* * * * *